United States Patent [19]

Tanabe et al.

[11] Patent Number: 4,701,567

[45] Date of Patent: Oct. 20, 1987

[54] PROCESS FOR PRODUCING 6,6'-DIHYDROXY-3,3,3',3'-TETRAMETHYL-1,1'-SPIROBIINDANE

[75] Inventors: Yoshimitsu Tanabe, Yokohama; Keizaburo Yamaguchi, Kawasaki; Yukihiro Yoshikawa, Zushi; Kenichi Sugimoto, Yokohama; Akihiro Yamaguchi, Kamakura, all of Japan

[73] Assignee: Mitsui Toatsu Chemicals, Inc., Tokyo, Japan

[21] Appl. No.: 878,687

[22] Filed: Jun. 26, 1986

[30] Foreign Application Priority Data

Jun. 28, 1985 [JP] Japan ................ 60-140406
Jul. 9, 1985 [JP] Japan ................ 60-149166

[51] Int. Cl.$^4$ ............................................ C07C 39/12
[52] U.S. Cl. ............................................. 568/719
[58] Field of Search ................. 568/719, 717, 721

[56] References Cited

U.S. PATENT DOCUMENTS 4,423,254 12/1983 Olah ................................ 568/719
4,605,789 8/1986 Silvis et al. ..................... 568/719

*Primary Examiner*—Werren B. Lone
*Attorney, Agent, or Firm*—Fisher, Christen & Sabol

[57] ABSTRACT

A novel process for producing 6,6'-dihydroxy-3,3,3',3'-tetramethyl-1,1'-spirobiindane of the formula (1)

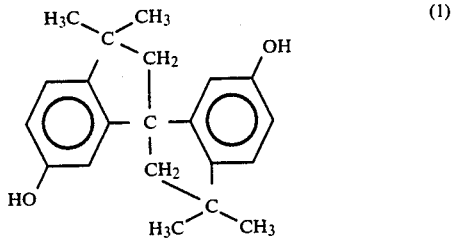

which comprises heat-treating 2,2-bis(4-hydroxyphenyl)propane in the presence of a superacid-type resin or a perfluoroalkanesulfonic acid.

7 Claims, No Drawings

PROCESS FOR PRODUCING 6,6'-DIHYDROXY-3,3,3',3'-TETRAMETHYL-1,1'-SPIROBIINDANE

BACKGROUND OF THE INVENTION

1. Field of the Invention

This invention relates to a novel process for producing 6,6'-dihydroxy-3,3,3',3'-tetramethyl-1,1'-spirobiindane. More specifically, it relates to a process for producing 6,6'-dihydroxy-3,3,3',3'-tetramethyl-1,1'-spirobiindane, which comprises heat-treating 2,2'-bis(4-hydroxyphenyl)propane in the presence of a superacid-type resin or a perfluoroalkanesulfonic acid.

2. Description of the Prior Art 6,6'-Dihydroxy-3,3,3',3'-tetramethyl-1,1'-spirobiindane is a very useful substance as a material for resins.

Known methods for the production of 6,6'-dihydroxy-3,3,3',3'-tetramethyl-1,1'-spirobiindane include, for example, treatment of 2,2-bis(4-hydroxyphenyl)propane in about two times its amount of sulfuric acid at 140° C. for 6 hours (U.S. Pat. No. 3,271,465), treatment of 2,2-bis(4-hydroxyphenyl)propane in a large excess of hydrobromic acid under reflux for 7 hours (J. Chem. Soc., Part I, pages 415–418, 1962), and treatment of 2,2-bis(4-hydroxyphenyl)propane with concentrated hydrochloric acid in an autoclave at 100° C. for 24 hours (U.S. Pat. No. 3,271,465).

The industrial practice of these methods is not rational because the yield is low, the use of a large amount of sulfuric acid or hydrobromic acid reduces the volume efficiency, an operation is required to treat the waste liquor and make it pollution-free, or equipment having corrosion resistnace is required.

SUMMARY OF THE INVENTION

It is an object of this invention to provide a novel process for producing 6,6'-dihydroxy-3,3,3',3'-tetramethyl-1,1'-spirobiindane.

It is another object of this invention to provide a process for producing the above compound in a good yield.

Still another object of this invention is to provide an industrial process for producing the above compound, which offers a solution to the aforesaid problems of the prior art such as pollution and the use of special reaction equipment.

The present inventors have extensively worked in order to achieve these objects, and have found that 6,6'-dihydroxy-3,3,3',3'-tetramethyl-1,1'-spirobiindane can be obtained rationally and efficiently by heat-treating 2,2-bis(4-hydroxyphenyl)propane as a starting material in the presence of a superacid-type resin or a perfluoroalkanesulfonic acid.

Thus, the present invention provides a process for producing 6,6'-dihydroxy-3,3,3',3'-tetramethyl-1,1'-spirobiindane which comprises heat-treating 2,2-bis(4-hydroxyphenyl)propane in the presence of a superacid-type resin or a perfluoroalkanesulfonic acid.

The desired compound can be easily produced by heat-treating 2,2-bis(4-hydroxyphenyl)propane in the presence of a superacid-type resin or a catalytic amount of a perfluoroalkanesulfonic acid by the process of this invention. When the superacid-type resin is used, it can be easily recovered from the reaction mixture by a filtration operation, and can be used in the next reaction. Accordingly, the process of this invention does not require waste liquor treatment, and can produce the desired compound rationally and efficiently. It is a very advantageous industrial process for producing 6,6'-dihydroxy-3,3,3',3'-tetramethyl-1,1'-spirobiindane.

DETAILED DESCRIPTION OF THE INVENTION

The final desired compound obtained by the process of this invention is 6,6'-dihydroxy-3,3,3',3'-tetramethyl-1,1'-spirobiindane of the following formula.

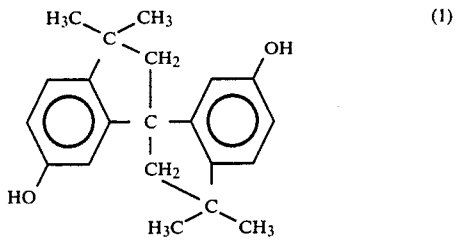

The starting material used in the process of this invention is 2,2'-bis(4-hydroxyphenyl)propane.

A solvent may be used in the process of this invention. Examples of the solvent include aromatic hydrocarbons such as benzene, toluene, xylene, ethylbenzene, trimethylbenzene, chlorobenzene, bromobenzene, anisole, naphthalene, biphenyl and diphenyl ether, and halogenated hydrocarbons such as 1,1'-dichloroethane, carbon tetrachloride, 1,2-dichloroethane, 1,1,1-trichloroethane, 1,1,2-trichloloroethane, 1,1,1,2-tetrachloroethane, 1,1,2,2-tetrachloroethane, 1,2-dichloroethylene, trichloroethylene and tetrachloroethylene. The amount of the solvent used is not particularly restricted. Usually, amounts 1 to 10 times the weight of the starting material suffice.

The process of this invention is carried out in the presence of a superacid-type resin or a perfluoroalkanesulfonic acid.

A perfluorosulfonic acid-type resin, Nafion H (a product of Du Pont), composed of sulfonyl fluoride vinyl ether and tetrafluoroethylene copolymer is an example of the superacid-type resin used in the process of this invention. This superacid-type resin (Nafion H) has a heat resistance of 200° C. or more, and can be reused. The superacid-type resin is used in an amount of 1 to 200% by weight, preferably 5 to 50% by weight, based on the weight of 2,2-bis(4-hydroxyphenyl)propane. The amount of the superacid-type resin, however, is not limited to these amounts, and the optimum amount may be properly determined by considering the amount of the product yielded and economy. The superacid-type resin used in the reaction is recovered from the reaction mixture by a filtration operation, and can be used in the subsequent reaction either as such or after it is regenerated.

The perfluoroalkanesulfonic acid used in the process of this invention is a sulfonic acid represented by the general formula $C_nF_{2n+1}SO_3H$ where n is an integer of 1 to 8. Specific examples trifluoromethanesulfonic acid ($CF_3SO_3H$), pentafluoroethanesulfonic acid ($C_2F_5SO_3H$), heptafluoropropanesulfonic acid ($C_3F_7SO_3H$), nonafluorobutanesulfonic acid ($C_4F_9SO_3H$), undecafluoropentanesulfonic acid ($C_5F_{11}SO_3H$), tridecafluorohexanesulfonic acid ($C_6F_{13}SO_3H$), pentadecafluoroheptanesulfonic acid ($C_7F_{15}SO_3H$), and heptadecafluorooctanesulfonic acid ($C_8F_{17}SO_3H$). The perfluoroalkanesulfonic acid is used in an amount of about 0.05 to 20% by weight, preferably about 0.1 to 10% by weight, more preferably about 0.1 to 1% by weight.

The reaction temperature is usually 50° to 200° C., preferably 60° to 160° C. The reaction time is 1 to 20 hours.

In a general embodiment of the process of this invention, 2,2-bis(4-hydroxyphenyl)propane and the superacid-type resin or the perfluoroalkanesulfonic acid are heat-treated optionally in the presence of a reaction solvent. The end point of the raction can be determined by monitoring the decrease of the starting material by high-performance liquid chromatography.

After the reaction, an aqueous solution of an alkali is added to the reaction mixture. This is done either after removing the superacid-type resin by filtration when it is used, or immediately when the perfluoroalkanesulfonic acid is used. As a result, the product is precipitated as an alkali metal salt. Alternatively, the solvent used optionally is evaporated, and the by-product phenol is removed by distillation under reduced pressure, after which an aqueous solution of an alkali is added to the reaction mixture to precipitate the product as an alkali metal salt. The alkali metal precipitated is then neutralized with a mineral acid to give a crude form of the desired product. Recrystallization of the crude product gives the final product in a purified form.

The following Examples illustrate the process of this invention more specifically.

EXAMPLE 1

A 1-liter separable flask was equipped with 250 g (1.1 moles) of 2,2'-bis(4-hydroxyphenyl)propane and 1 g of trifluoromethanesulfonic acid, and they were heated at 140° to 150° C. for 5 hours. After the reaction, the by-product phenol was recovered by distillation under reduced pressure. The reaction mixture was cooled, and 150 ml of isopropanol was added to dissolve the reaction mixture. Then, 510 g of a 9% aqueous solution of sodium hydroxide was added to precipitate cyrstals of the sodium salt of the product, followed by filtration. The filtration cake was heat-treated at 80° to 83° C. with 300 mg of a 25% aqueous solution of isopropanol for 30 minutes, cooled and filtered. The filtration cake was neutralized with hydrochloric acid in a 15% aqueous solution of isopropanol. The precipitated crystals were separated by filtration, washed with water, dried, azeotropically dehydrated in benzene, filtered, and dried to give 81.5 g of 6,6'-dihydroxy-3,3,3',3'-tetramethyl-1,1'-spirobiindane as white crystals.

Melting point: 215°–217° C.

| Elemental analysis values (%): | | |
|---|---|---|
| | C | H |
| Calculated | 81.82 | 7.79 |
| Found | 81.60 | 7.68 |

MS: 308 (M+), 293 (M-CH$_3$)+

EXAMPLE 2

A 1-liter separable flask was charged with 125 g (0.55 mole) of 2,2'-bis(4-hydroxyphenyl)propane, 1.2 g of trifluoromethanesulfonic acid and 375 ml of toluene, and they were heated under reflux for 9 hours. The reaction mixture was cooled, and immediately then toluene was evaporated. The by-product phenol was recovered by distillation under reduced pressure. The residue was worked up by the same operation as in Example 1 to give 39 g of 6,6'-dihydroxy-3,3,3',3'-tetramethyl-1,1'-spirobiindane as white crystals having a melting point of 215° to 217° C.

EXAMPLE 3

A 1-liter separable flask was charged with 125 g (0.55 mole) of 2,2'-bis(4-hydroxyphenyl)propane, 1.2 g of trifluoromethanesulfonic acid, and 375 ml of tetrachloroethylene, and they were heated under reflux for 7 hours. The reaction mixture was worked up by the same procedure as in Example 2 to give 40 g of 6,6'-dihydroxy-3,3,3',3'-tetramethyl-1,1'-spirobiindane as white crystals having a melting point of 215° to 217° C.

EXAMPLE 4

A 500 ml separable flask was charged with 125 g (0.55 mole) of 2,2'-bis(4-hydroxyphenyl)propane and 0.5 g of pentafluoroethanesulfonic acid, and they were heated at 140° to 150° C. for 6 hours. The reaction mixture was worked up by the same operation as in Example 1 to give 42 g of 6,6'-dihydroxy-3,3,3',3'-tetramethyl-1,1'-spirobiindane having a melting point of 215° to 217° C.

EXAMPLE 5

A 500 ml separable flask was charged with 125 g (0.55 mole) of 2,2'-bis(4-hydroxyphenyl)propane and 0.5 g of perfluoroheptanesulfonic acid, and they were heated at 140° to 150° C. for 5 hours. The reaction mixture was worked up by the same operation as in Example 1 to give 40 g of 6,6'-dihydroxy-3,3,3',3'-tetramethyl-1,1'-spirobiindane as white crystals having a melting point of 215° to 217° C.

EXAMPLE 6

A 2-liter separable flask was charged with 500 g (2.2 moles) of 2,2'-bis(4-hydroxyphenyl)propane and 0.5 g of trifluoromethanesulfonic acid, and they were heated at 150° to 160° C. for 8 hours. The reaction mixture was worked up by the same operation as in Example 1 to give 160 g of 6,6'-dihydroxy-3,3,3',3'-tetramethyl-1,1'-spirobiindane as white crystals having a melting point of 215° to 217° C.

EXAMPLE 7

Fifty grams of Nafion K (commercially available as K+-form from Du Pont) and 40 ml of 4N hydrochloric acid were stirred at room temperature for 4 hours. The mixture was filtered, and washed with distilled water until it became neutral. This operation was repeated four times further, and the product was dried at 80° to 90° C. under a reduced pressure of 10 mmHg to give a superacid-type resin Nafion H.

A 1-liter separable flask was charged with 250 g (1.1 moles) of 2,2-bis(4-hydroxyphenyl)propane and 12.5 g of the Nafion H, and they were stirred at 140° to 150° C. for 5 hours.

After the reaction, the Nafion H was separated by filtration from the reaction mixture at 60° C., and washed with a small amount of toluene. Toluene was evaporated from the mixture of the filtrate and the washing, and the by-product phenol was recovered from it by distillation under reduced pressure. The residue was then cooled, and 150 ml of isopropanol was added to dissolve it. The solution was then poured into 510 g of a 9% aqueous solution of sodium hydroxide to precipitate crystals of the sodium salt of the product. The mixture was filtered, and the filtration cake was heat-treated with 300 ml of a 25% aqueous solution of isopropanol at 80° to 83° C. for 30 minutes, cooled, and filtered. The filtration cake was neutralized with aqueous ammonia in a 15% aqueous solution of isopropanol. The precipitated crystals were separated by filtration, washed with water, dried, and azeotropically dehydrated in benzene, filtered, and dried to give 79 g of 6,6'-dihydroxy-3,3,3',3'-tetramethyl-1,1'-spirobiindane as white crystals.

Melting point: 215°–217° C.

| Elemental analysis values (%): | | |
| --- | --- | --- |
| | C | H |
| Calculated | 81.82 | 7.79 |
| Found | 81.52 | 7.83 |

MS: 308 (M+), 293 (M-CH$_3$)+

EXAMPLE 8

A 500 ml separable flask was charged with 125 g (0.55 mole) of 2,2-bis(4-hydroxyphenyl)propane and 6.3 g of Nafion H used and recovered in Example 7, and they were treated at 140° to 150° C. for 5 hours. The reaction mixture was worked up by the same operation as in Example 7 to give 39.5 g of 6,6'-dihydroxy-3,3,3',3'-tetramethyl-1,1'-spirobiindane as white crystals having a melting point of 215° to 217° C.

EXAMPLE 9

A 1-liter seaprable flask was charged with 125 g (0.55 mole) of 2,2'-bis(4-hydroxyphenyl)propane, 500 ml of toluene and 12.5 g of Nafion H, and they were treated under reflux for 10 hours with stirring. After the reaction, the reaction mixture was cooled and filtered to separate Nafion H. The residue was washed with a small amount of toluene, and then worked up by the same operation as in Example 7 to give 39 g of 6,6'-dihydroxy-3,3,3',3'-tetramethyl-11,1'-spirobiindane as white crystals having a melting point of 215° to 217° C.

EXAMPLE 10

A 1-liter separable flask was charged with 125 g (0.55 mole) of 2,2'-bis(4-hydroxyphenyl)propane, 500 ml of toluene and 12.5 g of Nafion H used and recovered in Example 9, and they were treated under reflux for 10 hours with stirring. After the reaction, the reaction mixture was cooled, and filtered to remove Nafion H. The residue was worked up by the same procedure as in Example 7 to give 39 g of 6,6'-dihydroxy-3,3,3',3'-tetramethyl-1,1'-spirobiindane as white crystals having a melting point of 215° to 217° C.

EXAMPLE 11

A 1-liter separable flask was charged with 125 g (0.55 mole) of 2,2'-bis(4-hydroxyphenyl)propane, 500 ml of trichloroethylene and 12.5 g of Nafion H and they were treated under reflux for 6 hours with stirring. After the reaction, the reaction mixture was cooled, and filtered to remove Nafion H. The residue was worked up by the same procedure as in Example 7 to give 40 g of 6,6'-dihydroxy-3,3,3',3'-tetramethyl-1,1'-spirobiindane as white crystals having a melting point of 215° to 217° C.

EXAMPLE 12

A 1-liter separable flask was charged with 125 g (0.55 mole) of 2,2'-bis(4-hydroxyphenyl)propane, 500 ml of 1,2-dichloroethane and 12.5 g of Nafion H and they were treated under reflux for 8 hours with stirring. After the reaction, the reaction mixture was cooled, and filtered to remove Nafion H. The residue was worked up by the same procedure as in Example 7 to give 37 g of 6,6'-dihydroxy-3,3,3',3'-tetramethyl-1,1'-spirobiindane as white crystals having a melting point of 215° to 217° C.

What is claimed is:

1. Process for producing 6,6'-dihydroxy-3,3,3',3'-tetramethyl-1,1'spirobiindane of the formula (1):

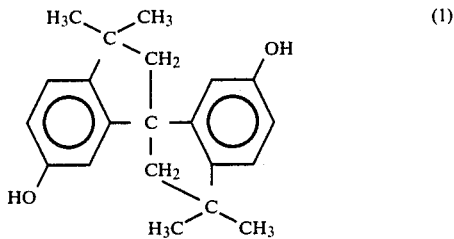

which comprises heat-treating 2,2-bis(4-hydroxyphenyl)propane at a temperature of 50° to 200° C. in the presence of a superacid-type resin.

2. The process as claimed in claim 1 wherein the heat-treatment is carried out in an organic solvent.

3. The process as claimed in claim 1 wherein the superacid-type resin is a perfluorosulfonic acid-type resin.

4. The process as claimed in claim 1 wherein the amount of the perfluorosulfonic acid is 0.1 to 10 percent by weight, based on the 2,2'-bis(4-hydroxyphenyl)propane.

5. The process as claimed in claim 1 wherein the amount of the perfluorosulfonic acid is 0.1 to 1 percent by weight, based on the 2,2'-bis(4-hydroxyphenyl)propane.

6. Process for producing 6,6'-dihydroxy-3,3,3',3'-tetramethyl-1,1'spirobiindane of the formula (1):

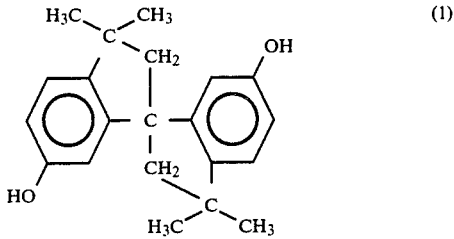

which comprises heat-treating 2,2-bis(4-hydroxyphenyl)propane at a temperature of 50° to 200° C. in the presence of 0.05 to 20 percent by weight, based on the 2,2'-bis(4-hydroxyphenyl)propane, of perfluoroalkanesulfonic acid.

7. The process as claimed as claim 6 wherein the perfluoroalkanesulfonic acid is a compound of the formula $C_nF_{2n+1}SO_3H$ wherein n is an integer of 1 to 8.

* * * * *